United States Patent
Barrott et al.

(10) Patent No.: US 11,051,630 B1
(45) Date of Patent: Jul. 6, 2021

(54) ROCKING BED BASE

(71) Applicants: Sarah Barrott, Chattanooga, TN (US); Rikel Barrott, Chattanooga, TN (US)

(72) Inventors: Sarah Barrott, Chattanooga, TN (US); Rikel Barrott, Chattanooga, TN (US)

( * ) Notice: Subject to any disclaimer, the term of this patent is extended or adjusted under 35 U.S.C. 154(b) by 296 days.

(21) Appl. No.: 16/292,419

(22) Filed: Mar. 5, 2019

(51) Int. Cl.
| | | |
|---|---|---|
| *A47C 21/00* | (2006.01) | |
| *A47C 31/00* | (2006.01) | |
| *A61G 7/005* | (2006.01) | |
| *A61D 3/00* | (2006.01) | |
| *A61G 7/018* | (2006.01) | |
| *A61M 21/02* | (2006.01) | |
| *A61M 21/00* | (2006.01) | |

(52) U.S. Cl.
CPC .......... *A47C 21/006* (2013.01); *A47C 21/003* (2013.01); *A47C 31/008* (2013.01); *A61D 3/00* (2013.01); *A61G 7/005* (2013.01); *A61G 7/018* (2013.01); *A61M 21/02* (2013.01); *A61M 2021/0022* (2013.01); *A61M 2205/3365* (2013.01); *A61M 2250/00* (2013.01)

(58) Field of Classification Search
CPC ... A47C 21/006; A47C 21/003; A47C 31/008; A61G 7/018; A61G 7/005; A61D 3/00; A61M 21/02; A61M 2250/00; A61M 2021/0022; A61M 2205/3365; A61H 1/003
See application file for complete search history.

(56) References Cited

U.S. PATENT DOCUMENTS

| | | | | |
|---|---|---|---|---|
| 2,350,563 A | | 6/1944 | Logan | |
| 3,210,778 A | * | 10/1965 | Robinson | A61G 7/008 5/607 |
| 3,638,248 A | * | 2/1972 | Silverglate | A47D 9/02 5/105 |
| 4,028,753 A | * | 6/1977 | Rios | A47D 9/02 5/108 |
| 4,152,795 A | | 5/1979 | Rodosta | |
| 4,277,857 A | * | 7/1981 | Svehaug | A61G 7/0573 5/108 |
| 4,752,980 A | * | 6/1988 | Nafte | A47D 9/04 5/108 |
| 4,934,997 A | * | 6/1990 | Skakas | A47D 7/04 5/101 |
| 5,040,253 A | * | 8/1991 | Cheng | A47C 20/041 5/616 |

(Continued)

FOREIGN PATENT DOCUMENTS

WO 2014007841 1/2014

*Primary Examiner* — Peter M. Cuomo
*Assistant Examiner* — Rahib T Zaman (57) ABSTRACT

The rocking bed base is configured for use with a mattress. The rocking bed base is configured to fit inside of the existing bed frame or replace the bed frame and box spring traditionally associated with a mattress. The rocking bed base comprises a pedestal, a mattress container, the mattress, and a personal data device. The mattress container attaches to the pedestal. The mattress is contained within the mattress container. The mattress container is motorized such that the mattress container will rhythmically rotate around an axis of rotation that is parallel to the major axis of the pedestal. The personal data device controls the rotation of the mattress container. The personal data device further controls the sleeping environment in the space around the rocking bed base.

16 Claims, 4 Drawing Sheets

(56) References Cited

U.S. PATENT DOCUMENTS

| | | | | |
|---|---|---|---|---|
| 5,228,155 A | * | 7/1993 | Shultz | A47D 9/02 |
| | | | | 5/109 |
| 5,404,603 A | * | 4/1995 | Fukai | A61G 7/001 |
| | | | | 5/609 |
| 5,625,913 A | * | 5/1997 | Singleton | A47C 21/006 |
| | | | | 5/430 |
| 6,682,495 B2 | | 1/2004 | Park | |
| 7,234,179 B2 | * | 6/2007 | Shaw | A61G 7/005 |
| | | | | 5/607 |
| 7,281,284 B2 | * | 10/2007 | Sims, Jr. | A47C 21/006 |
| | | | | 5/108 |
| 7,685,657 B1 | * | 3/2010 | Hernandez | A47D 9/02 |
| | | | | 5/109 |
| 8,789,220 B2 | * | 7/2014 | Flemister | A61G 7/005 |
| | | | | 5/108 |
| 2005/0091744 A1 | | 5/2005 | Mayyak | |
| 2009/0211022 A1 | | 8/2009 | Harding | |
| 2010/0325794 A1 | | 12/2010 | Chung | |
| 2017/0258241 A1 | | 9/2017 | Russell | |
| 2017/0318978 A1 | | 11/2017 | Flemister | |

* cited by examiner

ROCKING BED BASE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including beds for nursing, more specifically, a bed that rotates around a longitudinal axis. (A61G7008)

SUMMARY OF INVENTION

The rocking bed base is configured for use with a mattress. The rocking bed base is configured to fit inside of the existing bed frame or replace the bed frame and box spring traditionally associated with a mattress. The rocking bed base comprises a pedestal, a mattress container, the mattress, and a personal data device. The mattress container attaches to the pedestal. The mattress is contained within the mattress container. The mattress container is motorized such that the mattress container will rhythmically rotate around an axis of rotation that is parallel to the major axis of the pedestal. The personal data device controls the rotation of the mattress container. The personal data device further controls the sleeping environment in the space around the rocking bed base.

These together with additional objects, features and advantages of the rocking bed base will be readily apparent to those of ordinary skill in the art upon reading the following detailed description of the presently preferred, but nonetheless illustrative, embodiments when taken in conjunction with the accompanying drawings.

In this respect, before explaining the current embodiments of the rocking bed base in detail, it is to be understood that the rocking bed base is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the rocking bed base.

It is therefore important that the claims be regarded as including such equivalent construction insofar as they do not depart from the spirit and scope of the rocking bed base. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 5.

The rocking bed base 100 (hereinafter invention) is configured for use with a mattress 103. The invention 100 is configured to fit inside of the existing bed frame or replace the bed frame and box spring traditionally associated with a mattress 103. The invention 100 comprises a pedestal 101, a mattress 103 container 102, the mattress 103, and a personal data device 104. The mattress 103 container 102 attaches to the pedestal 101. The mattress 103 is contained within the mattress 103 container 102. The mattress 103 container 102 is motorized such that the mattress 103 container 102 will rhythmically rotate around an axis of rotation that is parallel to the major axis of the pedestal 101. The personal data device 104 controls the rotation of the mattress 103 container 102. The personal data device 104 further controls the sleeping environment in the space around the invention 100.

The mattress 103 is a cushion that is traditionally used for sleeping. The mattress 103 is a structure that is well-known and documented in our society.

Figure 1:
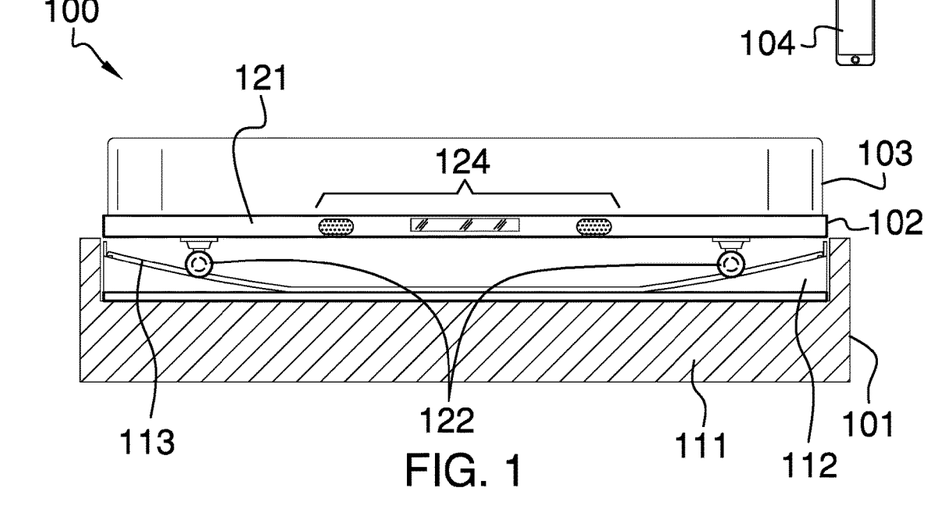
FIG. 1 is a front still view of an embodiment of the disclosure.
Figure 2:
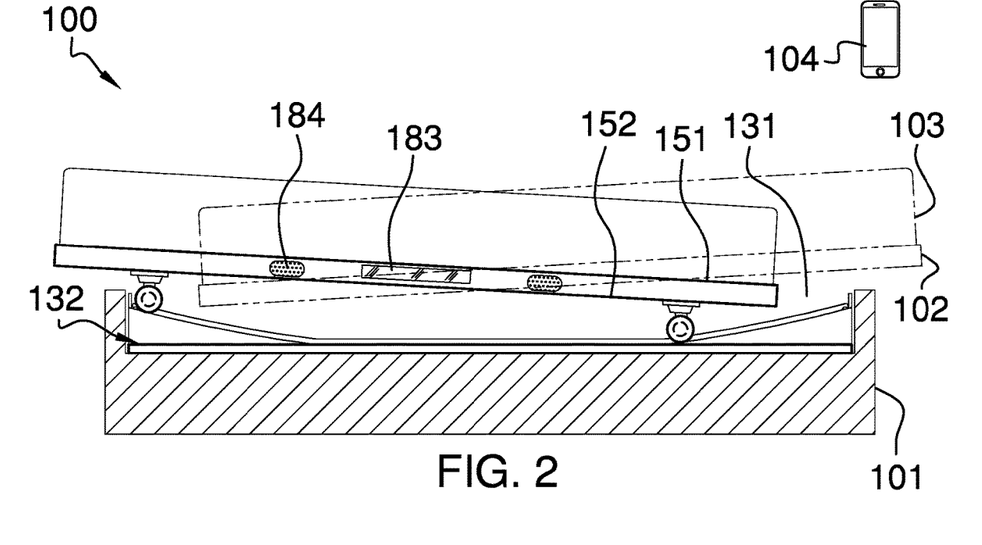
FIG. 2 is a front motion view of an embodiment of the disclosure.
Figure 3:
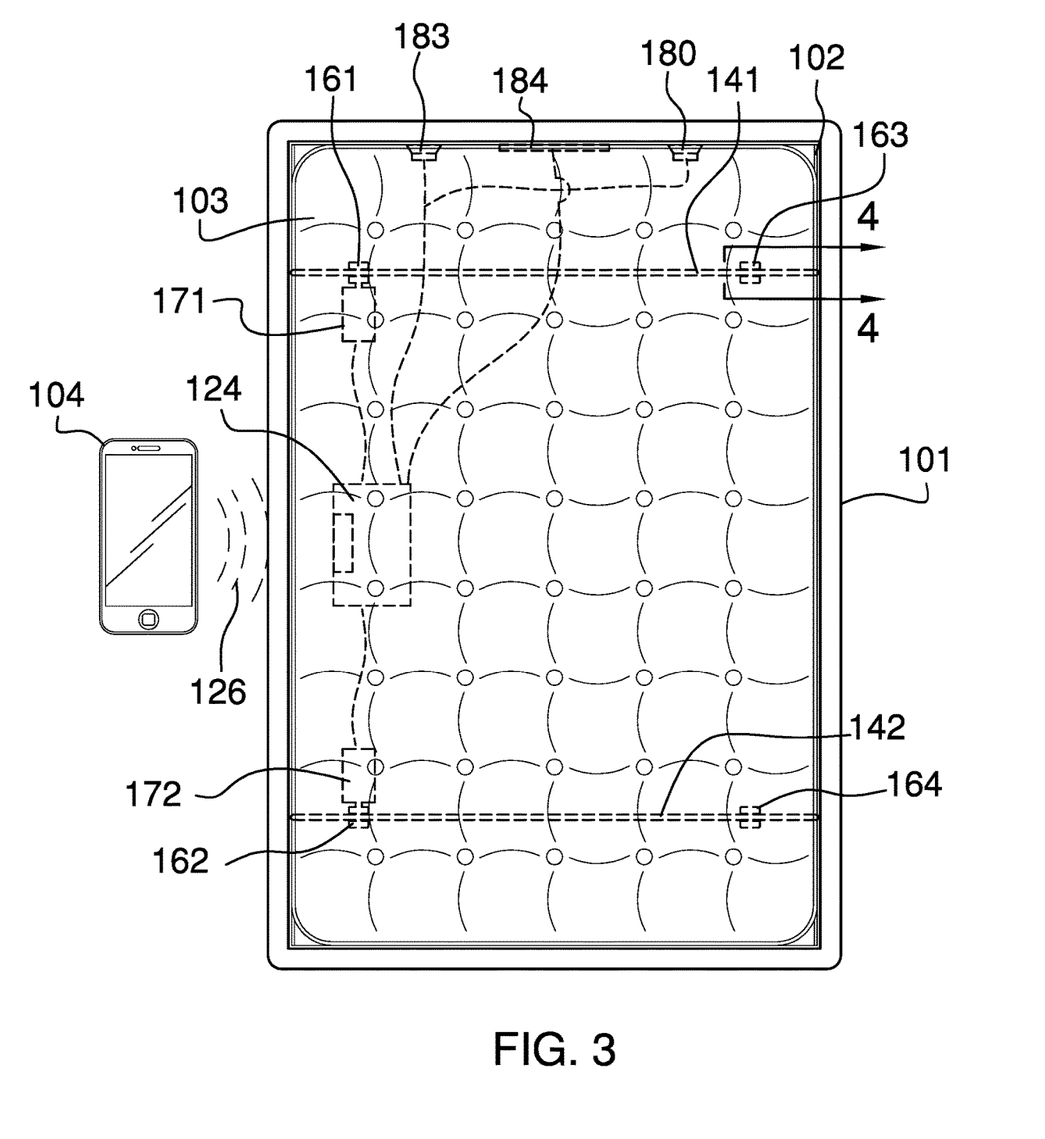
FIG. 3 is a top view of an embodiment of the disclosure.
Figure 4:
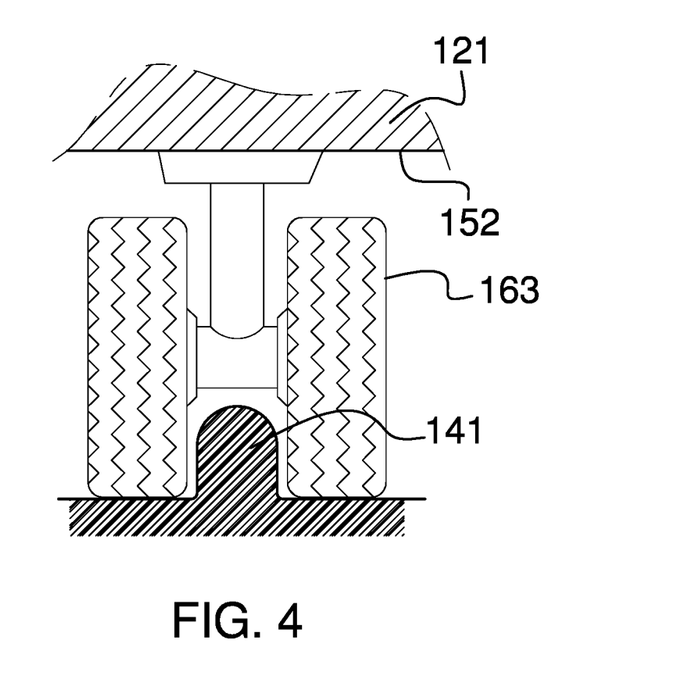
FIG. 4 is a detail view of an embodiment of the disclosure.
Figure 5:
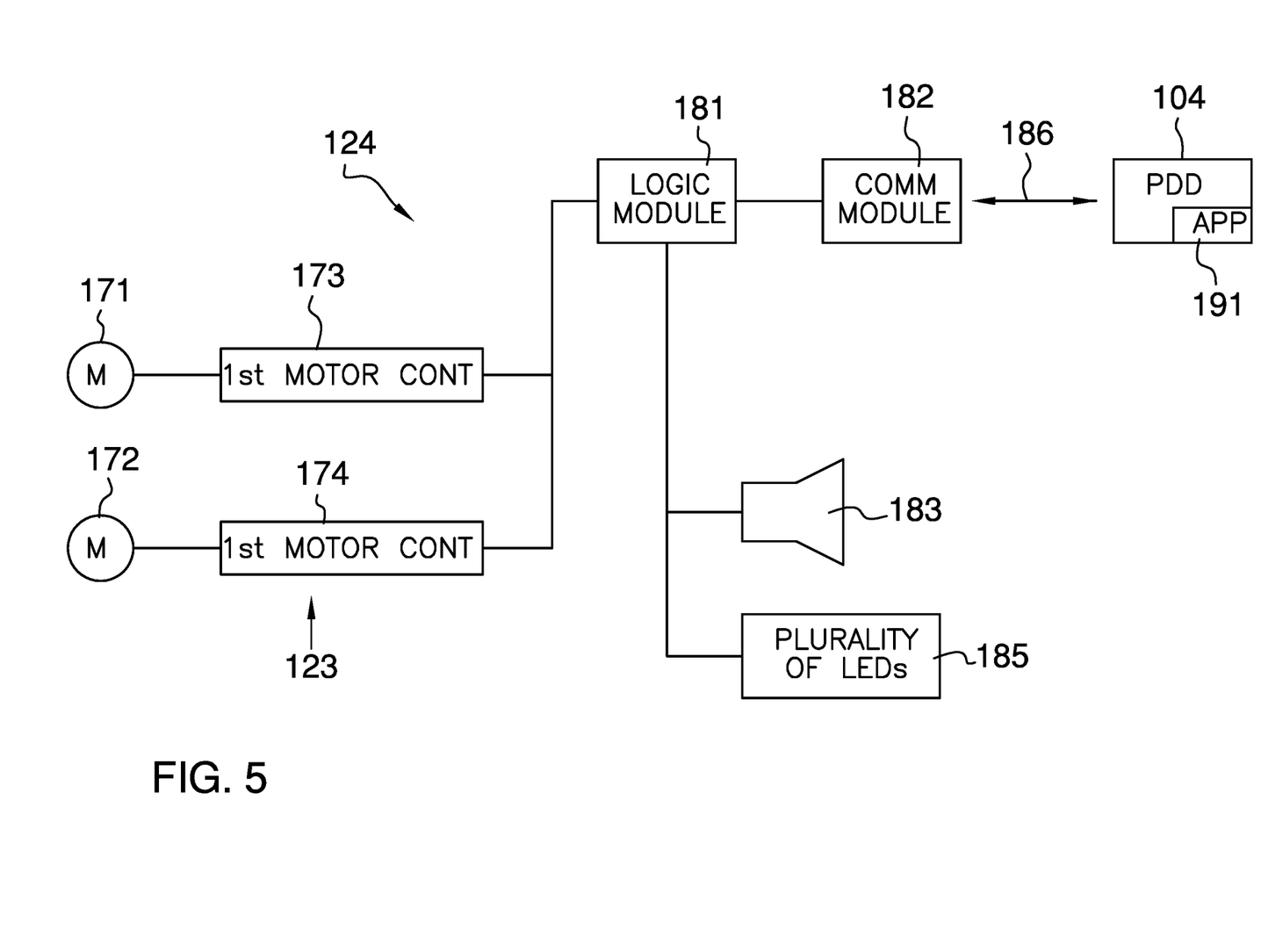
FIG. 5 is a block diagram of an embodiment of the disclosure.

The personal data device 104 is a programmable electrical device that provides data management and communication services through one or more functions referred to as an application 191. The application 191 is a set of logical operating instructions that are performed by the personal data device 104. The addition of an application 191 will provide increased functionality for the personal data device 104. This disclosure assumes that an application 191 exists for the purpose of interacting with the invention 100. Methods to design and implement an application 191 on a personal data device 104 are well known and documented in the electrical arts. In the first potential embodiment of the disclosure, the personal data device 104 sends instructions to the control circuit 124 regarding the operation of the plurality of motors 123, the lamp 183, and the speaker 184.

The pedestal 101 is a load-bearing structure. The pedestal 101 forms a load path between the combination of the mattress 103 container 102 and the mattress 103 and a supporting surface. The pedestal 101 comprises a pedestal 101 block 111, a pedestal pan 112, and a plurality of tracks 113.

The pedestal 101 block 111 is a prism-shaped structure. The pedestal 101 block 111 forms the last link in the load path that transfers the load of the mattress 103 container 102 and the mattress 103 to the supporting surface. The pedestal 101 block 111 has a rectangular block shape. The pedestal 101 block 111 is further defined with a major axis.

The pedestal 101 pan 112 is a negative space that is formed in the superior surface of the pedestal 101 block 111. The pedestal 101 pan 112 is a prism-shaped structure. The pedestal pan 112 has a rectangular block shape. The pedestal 101 pan 112 forms a cavity into which the mattress 103 container 102 inserts. The pedestal 101 pan 112 comprises a PP open face 131 and a PP closed face 132.

The PP open face 131 is the open face of the pan structure of the pedestal 101 pan 112 of the pedestal 101. The PP open face 131 is formed in the superior surface of the pedestal 101 block 111. The PP closed face 132 is the closed face of the pan structure of the pedestal 101 pan 112 of the pedestal 101. The PP closed face 132 is distal from the PP open face 131. The span of the length of the perimeter of the PP open face 131 is greater than the span of the length of the perimeter of the mattress 103. The span of the length of the perimeter of the PP open face 131 is greater than the span of the length of the perimeter of the mattress 103 container 102 such that the mattress 103 container 102 fits within the PP open face 131.

Each of the plurality of tracks 113 is a track that guides the motion of the mattress 103 container 102 within the pedestal 101 pan 112. Each of the plurality of tracks 113 is identical. Each of the plurality of tracks 113 mounts on the PP closed face 132 of the pedestal 101 pan 112. Each of the plurality of tracks 113 has a non-Euclidean prism shape. The curvature of each of the plurality of tracks 113 is set such that the mattress 103 container 102 will rotate around the major axis of the pedestal 101 block 111 when the mattress 103 container 102 moves along the direction of the plurality of tracks 113. The mattress 103 container 102 attaches to the pedestal 101 by attaching to the plurality of tracks 113. The plurality of tracks 113 comprises a first track 141 and a second track 142.

The first track 141 is a non-Euclidean shaft structure. The first track 141 attaches to the PP closed face 132 of the pedestal 101 pan 112. The first track 141 guides the movement of the first wheel 161 and the third wheel 163 of the plurality of wheels 122. The second track 142 is a non-Euclidean shaft structure. The second track 142 attaches to the PP closed face 132 of the pedestal 101 pan 112. The second track 142 guides the movement of the second wheel 162 and the fourth wheel 164 of the plurality of wheels 122. The second track 142 is identical to the first track 141. The track of the path formed by the second track 142 is parallel to the track of the path formed by the first track 141.

The mattress 103 container 102 contains the mattress 103. The mattress 103 container 102 is a pan structure that mounts on the pedestal 101. The mattress 103 container 102 mounts on the pedestal 101 such that the mattress 103 container 102 rotates within the pedestal 101. The mattress 103 sits in the mattress 103 container 102 such that the mattress 103 rotates with the mattress 103 container 102. The mattress 103 container 102 comprises a mattress 103 pan 121, a plurality of wheels 122, a plurality of motors 123, and a control circuit 124.

The mattress 103 pan 121 is a hollow prism-shaped structure. The mattress 103 pan 121 has a pan-shaped structure. The mattress 103 pan 121 comprises an MP open face 151 and an MP closed face 152. The MP open face 151 is the open face of the pan structure of the mattress 103 pan 121 of the mattress 103 container 102. The MP closed face 152 is the closed face of the pan structure of the mattress 103 pan 121 of the mattress 103 container 102. The MP closed face 152 is distal from the MP open face 151. The plurality of wheels 122 attaches to the exterior surface of the MP closed face 152.

The span of the length of the perimeter of the MP open face 151 is greater than the span of the length of the perimeter of the mattress 103 such that the mattress 103 fits within the perimeter of the MP open face 151. The span of the length of the perimeter of the PP open face 131 is greater than the span of the length of the perimeter of the MP closed face 152 such that the MP closed face 152 fits within the perimeter of the PP open face 131.

Each of the plurality of wheels 122 is a wheel that mounts on the exterior surface of the closed face of the pan structure of the mattress 103 pan 121. Each of the plurality of wheels 122 attaches to a track selected from the plurality of tracks 113. Each of the plurality of wheels 122 attaches to the selected track such that the selected track guides the motion of the selected wheel. The plurality of wheels 122 comprises a first wheel 161, a second wheel 162, a third wheel 163, and a fourth wheel 164.

The first wheel 161 is a rotating structure that attaches to the first track 141 such that the first track 141 guides the movement of the first wheel 161. The third wheel 163 is a rotating structure that attaches to the first track 141 such that the first track 141 guides the movement of the third wheel 163. The second wheel 162 is a rotating structure that attaches to the second track 142 such that the second track 142 guides the movement of the second wheel 162. The fourth wheel 164 is a rotating structure that attaches to the second track 142 such that the second track 142 guides the movement of the fourth wheel 164.

Each of the plurality of motors 123 is an electric motor. Each of the plurality of motors 123 attaches to a wheel selected from the plurality of wheels 122. Each of the plurality of motors 123 provides the motive forces required to move the mattress 103 pan 121 along the plurality of tracks 113. The plurality of motors 123 comprises a first motor 171 and a second motor 172.

The first motor 171 is an electric motor. The first motor attaches to the first wheel 161 such that the first motor 171 rotates the first wheel 161. The first motor 171 provides the motive forces to move the first wheel 161 and the third wheel 163 along the plurality of tracks 113. The first motor 171 further comprises a first motor control 173. The first motor control 173 is a motor controller. The first motor control 173 is operated by the control circuit 124. The first motor control 173 controls the speed of rotation of the first motor 171 and the first wheel 161. The first motor control 173 controls the direction of rotation of the first motor 171 and the first wheel 161.

The second motor 172 is an electric motor. The second motor 172 attaches to the second wheel 162 such that the second motor 172 rotates the second wheel 162. The second motor 172 provides the motive forces to move the second wheel 162 and the fourth wheel 164 along the plurality of tracks 113. The second motor 172 further comprises a second motor control 174. The second motor control 174 is a motor controller. The second motor control 174 is operated by the control circuit 124. The second motor control 174 controls the speed of rotation of the second motor 172 and the second wheel 162. The second motor control 174 controls the direction of rotation of the second motor 172 and the second wheel 162.

The control circuit 124 is an electrical circuit. The control circuit 124 installs in the mattress 103 pan 121. The control circuit 124 receives operating data and instructions from the personal data device 104. The control circuit 124 controls the operation of the plurality of motors 123. The control circuit 124 is an audio device that generates audible sounds. The control circuit 124 further forms a lamp 183 that illuminates the space around the mattress 103 container 102 and the mattress 103. The control circuit 124 further comprises a logic module 181, a communication module 182, a lamp 183, and a speaker 184.

The logic module 181 is a readily and commercially available programmable electronic device that is used to manage, regulate, and operate the control circuit 124. Depending on the specific design and the selected components, the logic module 181 can be a separate component within the control circuit 124 or the functions of the logic module 181 can be incorporated into another component within the control circuit 124.

The logic module 181 controls the operation of the first motor control 173 and the second motor control 174. The logic module 181 controls the operation of the lamp 183. The logic module 181 acts as an audio source that converts an audio file provided by the personal data device 104 into electrical signals. The logic module 181 transmits the generated electrical signals to the speaker 184.

The communication module 182 is a wireless electronic communication device that allows the logic module 181 to wirelessly communicate with a locally presented personal data device 104. Specifically the communication module 182 establishes a wireless communication link 186 between the control circuit 124 and the personal data device 104. In the first potential embodiment of the disclosure the communication module 182 supports a Bluetooth™ communication protocol.

The lamp 183 is an electrical circuit that illuminates the space around the mattress 103 container 102 and the mattress 103. In the first potential embodiment of the disclosure, the lamp 183 comprises a plurality of LEDs 185. Each of the plurality of LEDs 185 is a two-terminal semiconducting device used to generate illumination. The operation of the plurality of LEDs 185 is controlled by the logic module 181.

The speaker 184 is a transducer that is used as an audio device. The speaker 184 receives electrical signals from the logic module 181 and converts the electrical signals into audible sounds.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Application or App: As used in this disclosure, an application or app is a self-contained piece of software that is especially designed or downloaded for use with a personal data device.

Audio Device: As used in this disclosure, an audio device is a device that generates audible sound waves.

Audio File: As used in this disclosure, an audio file is a digital representation of a sound that is used to store a recording of the sound. Separate hardware is used to convert the digital representation of the sound into an audible sound.

Audio Source: As used in this disclosure, an audio source is a device that generates electrical signals that can be converted into audible sounds by a speaker.

Bluetooth™: As used in this disclosure, Bluetooth™ is a standardized communication protocol that is used to wirelessly interconnect electronic devices.

Cavity: As used in this disclosure, a cavity is an empty space or negative space that is formed within an object.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Center of Rotation: As used in this disclosure, the center of rotation is the point of a rotating plane that does not move with the rotation of the plane. A line within a rotating three-dimensional object that does not move with the rotation of the object is also referred to as an axis of rotation.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Correspond: As used in this disclosure, the term correspond is used as a comparison between two or more objects wherein one or more properties shared by the two or more objects match, agree, or align within acceptable manufacturing tolerances.

Cushion: As used in this disclosure a cushion is a pad or pillow formed from soft material used for resting, sleeping, or reclining.

Diode: As used in this disclosure, a diode is a two terminal semiconductor device that allows current flow in only one direction. The two terminals are called the anode and the cathode. Electric current is allowed to pass from the anode to the cathode.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Electric Motor: In this disclosure, an electric motor is a machine that converts electric energy into rotational mechanical energy. An electric motor typically comprises a stator and a rotor. The stator is a stationary hollow cylindrical structure that forms a magnetic field. The rotor is a magnetically active rotating cylindrical structure that is coaxially mounted in the stator. The magnetic interactions between the rotor and the stator physically causes the rotor to rotate within the stator thereby generating rotational mechanical energy. This disclosure assumes that the power source is an externally provided source of DC electrical power. The use of DC power is not critical and AC power can be used by exchanging the DC electric motor with an AC motor that has a reversible starter winding.

Force of Gravity: As used in this disclosure, the force of gravity refers to a vector that indicates the direction of the pull of gravity on an object at or near the surface of the earth.

Form Factor: As used in this disclosure, the term form factor refers to the size and shape of an object.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Illumination: As used in this disclosure, light refers to electromagnetic radiation contained with an area. Illumination is a synonym for light, particularly in cases where a measure of the amount of visible electromagnetic radiation in a space is called for.

Inferior: As used in this disclosure, the term inferior refers to a directional reference that is parallel to and in the same direction as the force of gravity when an object is positioned or used normally.

Lamp: As used in this disclosure, a lamp is an electrical device that generates (typically visible) electromagnetic radiation.

LED: As used in this disclosure, an LED is an acronym for a light emitting diode. A light emitting diode is a diode that is also a light source. Because of close operational correspondence of the function of the cathode and anode of an organic LEDs and the cathode and anode of a semiconductor LED, organic LEDs are included in this definition.

Load: As used in this disclosure, the term load refers to an object upon which a force is acting or which is otherwise absorbing energy in some fashion. Examples of a load in this sense include, but are not limited to, a mass that is being moved a distance or an electrical circuit element that draws energy. The term load is also commonly used to refer to the forces that are applied to a stationary structure.

Load Path: As used in this disclosure, a load path refers to a chain of one or more structures that transfers a load generated by a raised structure or object to a foundation, supporting surface, or the earth.

Logic Module: As used in this disclosure, a logic module is a readily and commercially available electrical device that is programmable and that accepts digital and analog inputs, processes the digital and analog inputs according to previously stored instruction and provides the results of these instructions as digital or analog outputs.

Major and Minor Axes: As used in this disclosure, the major and minor axes refer to a pair of perpendicular axes that are defined within a structure. The length of the major axis is always greater than or equal to the length of the minor axis. The major axis is always the longest diameter of the structure. The major and minor axes intersect at the center of the structure. The major axis is always parallel to an edge of a rectangular or rectilinear structure.

Motor: As used in this disclosure, a motor refers to the method of transferring energy from an external power source into rotational mechanical energy.

Motor Controller: As used in this disclosure, a motor controller is an electrical device that is used to control the rotational speed, or simply the speed of the motor, and the direction of rotation of an electric motor. Motor controllers will generally receive one or more inputs which are used determine the desired rotational speed and direction of rotation of the electric motor.

Negative Space: As used in this disclosure, negative space is a method of defining an object through the use of open or empty space as the definition of the object itself, or, through the use of open or empty space to describe the boundaries of an object.

Non-Euclidean Prism: As used in this disclosure, a non-Euclidean prism is a prism structure wherein the center axis of the prism lies on a non-Euclidean plane.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Pan: As used in this disclosure, a pan is a hollow and prism-shaped containment structure. The pan has a single open face. The open face of the pan is often, but not always, the superior face of the pan. The open face is a surface selected from the group consisting of: a) an end of the prism structure that forms the pan; and, b) a lateral face of the prism structure that forms the pan.

PDD: As used in this disclosure, PDD is an acronym for personal data device.

Pedestal: As used in this disclosure, a pedestal is an intermediary load bearing structure that that transfers a load path between a supporting surface and an object, structure, or load.

Perimeter: As used in this disclosure, a perimeter is one or more curved or straight lines that bounds an enclosed area on a plane or surface. The perimeter of a circle is commonly referred to as a circumference.

Personal Data Device: As used in this disclosure, a personal data device is a handheld logical device that is used for managing personal information and communication. Examples of personal data device include, but are not limited to, cellular phones, tablets, and smartphones.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Rhythm: As used in this disclosure, a rhythm refers to a pattern that repeats at regular intervals.

Speaker: As used in this disclosure, a speaker is an electrical transducer that converts an electrical signal into an audible sound.

Superior: As used in this disclosure, the term superior refers to a directional reference that is parallel to and in the opposite direction of the force of gravity when an object is positioned or used normally.

Supporting Surface: As used in this disclosure, a supporting surface is a horizontal surface upon which an object is placed and to which the load path of the object is transferred. This disclosure assumes that an object placed on the supporting surface is in an orientation that is appropriate for the normal or anticipated use of the object.

Track: As used in this disclosure, a track is a structural relationship between a first object and a second object that serves a purpose selected from the group consisting of: 1) fastening the second object to the first object; 2) controlling the path of motion of the first object relative to the second object in at least one dimension and in a maximum of two dimensions; or, 3) a combination of the first two elements of this group.

Tradition: As used in this disclosure, a tradition refers to: 1) a set of thoughts or expectations regarding a subject or object; or, 2) a method of using an object; that, 3) is perceived to be widely or commonly shared across a population of people; and that, 4) is perceived to be widely or commonly shared across at least two generations within the population of people.

Transducer: As used in this disclosure, a transducer is a device that converts a physical quantity, such as pressure or brightness into an electrical signal or a device that converts an electrical signal into a physical quantity.

Wheel: As used in this disclosure, a wheel is a circular object that revolves around an axle or an axis and is fixed below an object to enable it to move easily over the ground. For the purpose of this disclosure, it is assumed that a wheel can only revolve in a forward and a backward direction. Wheels are often further defined with a rim and spokes. Spokes are also commonly referred to as a wheel disk.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A rocking bed base comprising:
a pedestal, a mattress container, the mattress, and a personal data device;
wherein the mattress container attaches to the pedestal;
wherein the pedestal is further defined with a major axis;
wherein the mattress is contained within the mattress container;
wherein the personal data device controls the operation of the rocking bed base;
wherein the mattress container is motorized such that the mattress container will rhythmically rotate around an axis of rotation that is parallel to the major axis of the pedestal;
wherein the personal data device is a programmable electrical device;
wherein the personal data device controls the rotation of the mattress container;
wherein the pedestal is a load-bearing structure;
wherein the pedestal forms a load path between the combination of the mattress container and the mattress and a supporting surface;
wherein the mattress container is a pan structure that mounts on the pedestal;
wherein the mattress container mounts on the pedestal such that the mattress container rotates within the pedestal;
wherein the mattress sits in the mattress container such that the mattress rotates with the mattress container;
wherein the pedestal comprises a pedestal block, a pedestal pan, and a plurality of tracks;
wherein the pedestal pan is formed in the pedestal block;
wherein the plurality of tracks mount in the pedestal pan.

2. The rocking bed base according to claim 1
wherein the mattress container comprises a mattress pan, a plurality of wheels, a plurality of motors, and a control circuit;
wherein each of the plurality of motors attaches to a wheel selected from the plurality of wheels;
wherein each of the plurality of wheels attaches to the mattress pan;
wherein the control circuit attaches to the mattress pan.

3. The rocking bed base according to claim 2
wherein each of the plurality of wheels attaches to a track selected from the plurality of tracks;
wherein each of the plurality of wheels attaches to the selected track such that the selected track guides the motion of the selected wheel.

4. The rocking bed base according to claim 3
wherein the pedestal block is a prism-shaped structure;
wherein the pedestal block forms the last link in the load path that transfers the load of the mattress container and the mattress to the supporting surface;
wherein the pedestal block has a rectangular block shape;
wherein the pedestal block is further defined with the major axis.

5. The rocking bed base according to claim 4
wherein the pedestal pan is a negative space that is formed in the superior surface of the pedestal block;
wherein the pedestal pan is a prism-shaped structure;
wherein the pedestal pan has a rectangular block shape;
wherein the mattress container inserts into the pedestal pan.

6. The rocking bed base according to claim 5 wherein the pedestal pan comprises a pedestal pan, hereinafter PP, open face and a PP closed face; wherein the PP open face is the open face of the pan structure of the pedestal pan of the pedestal; wherein the PP open face is formed in the superior surface of the pedestal block; wherein the PP closed face is the closed face of the pan structure of the pedestal pan of the pedestal; wherein the PP closed face is distal from the PP open face; wherein the span of the length of the perimeter of the PP open face is greater than the span of the length of the perimeter of the mattress; wherein the span of the length of the perimeter of the PP open face is greater than the span of the length of the perimeter of the mattress container such that the mattress container fits within the PP open face.

7. The rocking bed base according to claim 6
wherein each of the plurality of tracks is a track that guides the motion of the mattress container within the pedestal pan;
wherein each of the plurality of tracks is identical;
wherein each of the plurality of tracks mounts on the PP closed face of the pedestal pan;
wherein each of the plurality of tracks has a non-Euclidean prism shape;
wherein the mattress container attaches to the pedestal by attaching to the plurality of tracks;
wherein the curvature of each of the plurality of tracks is set such that the mattress container will rotate around the major axis of the pedestal block when the mattress container moves along the direction of the plurality of tracks.

8. The rocking bed base according to claim 7
wherein the plurality of tracks comprises a first track and a second track;
wherein the first track is a non-Euclidean shaft structure;
wherein the first track attaches to the PP closed face of the pedestal pan;
wherein the second track is a non-Euclidean shaft structure;
wherein the second track attaches to the PP closed face of the pedestal pan;
wherein the second track is identical to the first track;
wherein the track of the path formed by the second track is parallel to the track of the path formed by the first track.

9. The rocking bed base according to claim 8
wherein the mattress pan is a hollow prism-shaped structure;
wherein the mattress pan has a pan-shaped structure.

10. The rocking bed base according to claim 9 wherein the mattress pan comprises a Mattress Pan, hereinafter MP, open face and an MP closed face; wherein the MP open face is the open face of the pan structure of the mattress pan of the mattress container; wherein the MP closed face is the closed face of the pan structure of the mattress pan of the mattress container; wherein the MP closed face is distal from the MP open face; wherein the plurality of wheels attaches to the exterior surface of the MP closed face; wherein the span of the length of the perimeter of the MP open face is greater than the span of the length of the perimeter of the mattress such that the mattress fits within the perimeter of the MP open face; wherein the span of the length of the perimeter of the PP open face is greater than the span of the length of the perimeter of the MP closed face such that the MP closed face fits within the perimeter of the PP open face.

11. The rocking bed base according to claim 10 wherein each of the plurality of wheels mounts on the exterior surface of MP closed face of the pan structure of the mattress pan.

12. The rocking bed base according to claim 11
wherein the plurality of wheels comprises a first wheel, a second wheel, a third wheel, and a fourth wheel;
wherein the first wheel is a rotating structure that attaches to the first track such that the first track guides the movement of the first wheel;
wherein the third wheel is a rotating structure that attaches to the first track such that the first track guides the movement of the third wheel;
wherein the second wheel is a rotating structure that attaches to the second track such that the second track guides the movement of the second wheel;
wherein the fourth wheel is a rotating structure that attaches to the second track such that the second track guides the movement of the fourth wheel.

13. The rocking bed base according to claim 12
wherein the first track guides the movement of the first wheel and the third wheel of the plurality of wheels;
wherein the second track guides the movement of the second wheel and the fourth wheel of the plurality of wheels.

14. The rocking bed base according to claim 13
wherein each of the plurality of motors is an electric motor;
wherein each of the plurality of motors attaches to a wheel selected from the plurality of wheels;
wherein each of the plurality of motors provides the motive forces required to move the mattress pan along the plurality of tracks.

15. The rocking bed base according to claim 14
wherein the plurality of motors comprises a first motor and a second motor;
wherein the first motor is an electric motor;
wherein the first motor attaches to the first wheel such that the first motor rotates the first wheel;
wherein the first motor provides the motive forces to move the first wheel and the third wheel along the plurality of tracks;
wherein the first motor further comprises a first motor control;
wherein the first motor control is a motor controller;
wherein the first motor control is operated by the control circuit;
wherein the first motor control controls the speed of rotation of the first motor and the first wheel;
wherein the first motor control controls the direction of rotation of the first motor and the first wheel;
wherein the second motor is an electric motor;
wherein the second motor attaches to the second wheel such that the second motor rotates the second wheel;
wherein the second motor provides the motive forces to move the second wheel and the fourth wheel along the plurality of tracks;
wherein the second motor further comprises a second motor control;
wherein the second motor control is a motor controller;
wherein the second motor control is operated by the control circuit;
wherein the second motor control controls the speed of rotation of the second motor and the second wheel;
wherein the second motor control controls the direction of rotation of the second motor and the second wheel.

16. The rocking bed base according to claim 15 wherein the control circuit is an electrical circuit;
wherein the control circuit receives operating data and instructions from the personal data device;
wherein the control circuit further comprises a logic module, a communication module, a lamp, and a speaker;

wherein the logic module is a readily and programmable electronic device;

wherein the logic module controls the operation of the first motor control and the second motor control;

wherein the logic module controls the operation of the lamp;

wherein the logic module acts as an audio source that converts an audio file provided by the personal data device into electrical signals;

wherein the logic module transmits the generated electrical signals to the speaker;

wherein the communication module is a wireless electronic communication device that allows the logic module to wirelessly communicate with a personal data device;

wherein the communication module establishes a wireless communication link between the control circuit and the personal data device;

wherein the lamp is an electrical circuit that illuminates the space around the mattress container and the mattress;

wherein the lamp comprises a plurality of LEDs;

wherein the operation of the plurality of LEDs is controlled by the logic module;

wherein the speaker is a transducer that is used as an audio device;

wherein the speaker receives electrical signals from the logic module and converts the electrical signals into audible sounds.

* * * * *